United States Patent [19]

Ogawa et al.

[11] Patent Number: 4,718,998

[45] Date of Patent: Jan. 12, 1988

[54] ELEMENT FOR ELECTROPHORESIS

[75] Inventors: Masashi Ogawa; Naohiko Sugimoto, both of Saitama, Japan

[73] Assignee: Fuji Photo Film Co., Ltd., Kanagawa, Japan

[21] Appl. No.: 52,579

[22] Filed: May 19, 1987

[30] Foreign Application Priority Data

May 20, 1986 [JP] Japan ................................ 61-115422
May 20, 1986 [JP] Japan ................................ 61-115423

[51] Int. Cl.[4] ...................... G01N 27/26; B01D 17/06
[52] U.S. Cl. .............................. 204/299 R; 204/182.8; 428/516; 428/483; 428/412; 428/518
[58] Field of Search ...................... 204/299 R, 182.8; 428/516, 518, 520, 483

[56] References Cited

U.S. PATENT DOCUMENTS 3,594,263  7/1971  Dwyer et al. ............... 428/412 X
4,415,428  11/1983 Nochumson et al. ....... 204/182.8 X
4,548,869  10/1985 Ogawa et al. ............... 428/483 X

FOREIGN PATENT DOCUMENTS 113700  7/1984  European Pat. Off. ........ 204/299 R

Primary Examiner—John F. Niebling
Assistant Examiner—John S. Starsiak, Jr.
Attorney, Agent, or Firm—Jules E. Goldberg

[57] ABSTRACT

An element for electrophoresis suitably employable for analysis of biopolymers such as proteins, as well as for determination of base sequence of DNA, RNA, their fragments, and their derivatives, which comprises a plastic film, a layer for electrophoresis comprising an aqueous polyacrylamide gel, an adhesive layer containing gelatin and optionally a film-forming polymer and/or fine particles, and a plastic film.

13 Claims, No Drawings

ELEMENT FOR ELECTROPHORESIS

BACKGROUND OF THE INVENTION

1. Field of the invention

This invention relates to an element for electrophoresis, and more particularly relates to an element for electrophoresis suitably employable for analysis of biopolymers such as proteins, as well as for determination of base sequence of DNA, RNA, their fragments, and their derivatives.

2. Description of prior art

For the analysis of biopolymers such as proteins, or for the determination of base sequence of DNA or RNA, the electrophoresis can be carried out in the following manner.

A membrane medium for electrophoresis prepared by coating or casting a membrane-forming material such as agar, cellulose, cellulose acetate, starch, silica gel or polyacrylamide gel over a support such as a glass plate or a transparent plastic sheet (or film) is impregnated with a buffer solution; on the medium is applied a substance to be analyzed (sample); the applied sample is developed (or resolved) on or in the medium by applying a voltage between the both ends of the support; the developed substance is dyed thereon; and then the dyed sample is measured on the optical density to quantitatively determine the developed components of the sample.

Details of electrophoresis and the element therefor are given in "Experimental Text for Electrophoresis (5th revision)" edited by Electrophoresis Society of Japan (Bunkodo, 1975), "Modern Electrophoresis" edited by Aoki Nagai (Hirokawa Shoten, 1973), etc.

Recently, the electrophoresis has been frequently employed to analyze substances originating from a living body; for instance, the analyses of proteins originating from a living body are generally performed in the course of biochemical analysis for diagnosis. The determinations of base sequences of DNA or RNA are also performed in the course of the study in the genetic engineering technology.

As the membrane or sheet for electrophoresis, a filter paper was previously employed, but recently an agarose membrane or a polyacrylamide gel membrane (or medium) has been employed from the viewpoints of their advantageous properties. Particularly, the polyacrylamide gel membrane showing a molecular sieve function is widely used recently. More particularly, in the method for determination of base sequence of DNA, RNA, their fragments, and their derivatives according to post-label method, a procedure of slab electrophoresis using a polyacrylamide gel membrane has become essential.

The polyacrylamide gel membrane can be prepared by crosslinking polymerization of a monomer such as acrylamide and a two-functional crosslinking agent such as N,N'-methylenebisacrylamide under an oxygen-free condition in the presence of water and a polymerization catalyst. In the course of the preparation of the polyacrylamide gel membrane, a modifier such as an anionic surfactant, urea or formamide is be incorporated into the membrane in certain cases.

Since the polymerization reaction for the preparation of polyacrylamide is a radical crosslinking polymerization reaction as described above, the polymerization can be easily inhibited by the presence of oxygen. Therefore, the gel membrane should be prepared in the absence of oxygen. For this reason, a polyacrylamide gel membrane is generally prepared by a process involving: introducing an aqueous solution (gel-forming solution or gel solution) containing acrylamide, a cross-linking agent and a polymerization catalyst into a cell formed between two glass plates with a certain clearance (e.g., 0.3–1 mm); sealing the gel-forming solution from oxygen; and causing the crosslinking polymerization to prepare the desired gel membrane.

The polyacrylamide gel membrane prepared as above is employed for electrophoresis. For example, the electrophoresis for analysis of biopolymers such as proteins is performed in the manner such as described below.

The prepared polyacrylamide gel is horizontally or vertically placed for performing slab electrophoresis. The electrophoresis is performed for a certain period of time under predetermined conditions, and the desired analysis of the components originating from a living body is done after dyeing the electrophoresed gel membrane with, for instance, Ponceau 3R (Ciba-Geigy), Coomassie Brilliant Blue G-250 (ICI), or silver.

Since the study in the genetic engineering technology has advance recently, quick determination of the base sequence of DNA, etc. is highly desired. The polyacrylamide gel membrane prepared as above is also employed for electrophoresis for determination of base sequence of DNA in the manner such as described below.

The polyacrylamide gel membrane is vertically placed in the form of being sandwiched between the glass plates, and in the first place a pre-electrophoresis procedure is carried out. Then, a certain amount of a sample (e.g., $^{32}$P-labeled DNA cleaved by Maxam-Gilbert method) is introduced into sample slots provided on the membrane, and electrophoresis is carried out. After the electrophoresis is carried out for a certain period of time (e.g., approx. 6–12 hours), one glass plate is removed carefully. Then, the exposed gel membrane is covered with a polymer film such as a poly(vinylidene chloride) film and subjected to an autoradiographic process. The autoradiographic process is carried out by the following procedures: a radiographic film and an intensifying screen are superposed successively on the film covering the gel membrane, whereby exposing the radiographic film to the gel membrane at a low temperature (e.g., −80° C.) for a certain period of time (e.g., approx. 10–20 hours). After completion of the exposing procedure, the radiographic film is developed, and the resolved pattern reproduced on the film is studied for determination of the base sequence of DNA, etc.

Since the autoradiographic process requires a long period of time as described above, it has been desired that the operational period be shortened. Moreover, enhancement of resolution accuracy in the detection of the resolved pattern is desired.

The above procedures employing glass plates are disadvantageous because the glass plate is easily breakable and rather heavy and hence careful handling is required. Thus, those procedures employing glass plates are not advantageously utilized to prepare the polyacrylamide gel membrane in a mass scale.

For the reason described above, it has been desired that the the glass plate for supporting the polyacrylamide gel membrane is replaced with a light-weight plastic material support such as a polyethylene terephthalate (PET) sheet. However, in spite of the use of a plastic material support, poor adhesion between the gel membrane and the plastic material supports are usually hydrophobic. Even if the surface of the plastic material support is made hydrophilic, or if the hydrophilic plastic material support is used, the adhesion between the gel membrane and the plastic material support is not on a satisfactory level.

Further, the gel membrane is apt to separate from the support in the above procedure even in the case of employing the glass plate support. Therefore, these procedures require highly skilled operation to prevent the separation of the gel membrane from the support. The poor affinity of a plastic material support to the polyacrylamide gel membrane makes it more difficult to handle the element for electrophoresis without separation of the support from the gel membrane.

SUMMARY OF THE INVENTION

An object of the present invention is to provide an element for electrophoresis which is improved in the adhesion between a plastic material support (plastic film or sheet) and an electrophoresis layer (i.e., polyacrylamide gel membrane).

Another object of the present invention is to provide an element for electrophoresis which is substantially free from separation of the electrophoresis layer from the support in the following stages such as a post-treatment stage in an aqueous solution and a subsequent drying stage.

There is provided by the present invention an element for electrophoresis comprising:
(I) a plastic film;
(II) a medium layer for electrophoresis comprising an aqueous polyacrylamide gel formed by crosslinking polymerization of an acrylamide compound and a crosslinking agent in the presence of water;
(III) an adhesive layer containing gelatin; and
(IV) a plastic film,
which are superposed in order.

The element for electrophoresis of the invention is highly resistant to separation between one of the plastic films serving as a support and the electrophoresis layer in a variety of the stages. Accordingly, the electrophresis layer is hardly broken in the analytical procedure, and the handling of the element is satisfactorily easy.

Moreover, an electrophoresis element of the invention can be prepared by forming an electrophoresis layer on an adhesive layer which is formed on a horizontally arranged plastic film (support) and covering the layer with other plastic film. Therefore, the element for electrophoresis of the invention can be advantageously prepared in a mass scale.

DETAILED DESCRIPTION OF THE INVENTION

An element for electrophoresis of the present invention has two layers of plastic material (i.e., plastic films) provided on both sides of the element. One may serve as a support, while the other may serve as a covering film. The plastic film includes a variety of polymer materials in the form of sheet (the term "sheet" includes film and plate). Examples of the polymer materials include polyethylene terephthalate, polycarbonate of Bisphenol A, polyvinyl chloride, vinylidene chloride - vinyl chloride copolymer, polymethyl methacrylate, polyethylene, polypropylene, cellulose acetates, and cellulose acetate propionate. Preferred is a polyethylene terephthalate sheet.

The surface of the plastic film employed in the invention can be made hydrophilic. Known methods for making a surface of a polymer material hydrophilic such as irradiation of ultraviolet rays, glow discharge treatment, corona discharge treatment, flame treatment, irradiation of electron radiation, chemical etching can be utilized.

The plastic film generally has a thickness in the range of approx. 4 to 500 $\mu$m, preferably not larger than approx. 300 $\mu$m. In the case of using the plastic film as a support, the thickness thereof is desired to be not less than approx. 50 $\mu$m.

On the plastic film, an aqueous gel layer (i.e., electrophoresis layer) is provided. In this case, the plastic film serves as a covering film.

The aqueous gel medium layer is now described in more detail.

The aqueous gel layer (may be referred to herein as "gel membrane") employed in the invention is a layer consisting essentially of an aqueous polyacrylamide gel formed by crosslinking polymerization of an acrylamide compound and a crosslinking agent in the presence of water.

For the preparation of the polyacrylamide gel membrane, an acrylamide compound and a crosslinking agent are dissolved or dispersed in water to prepare an aqueous solution or an aqueous dispersion, wherein the crosslinking reaction is carried out to form an aqueous polyacrylamide gel membrane. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term "aqueous medium" is used to include both a simple water as well as an aqueous mixture of water and an organic solvent, the organic solvent being optionally added.

Examples of the acrylamide compound employable in the present invention include acrylamide and its homologues such as N-methylacrylamide, N,N-dimethylacrylamide, N-(hydroxymethyl)acrylamide and diacetonacrylamide, as well as methacrylamide and its homologes. These compounds can be employed independently or in combination. Acrylamide is most preferred among these acrylamide compounds, and this acrylamide can be also preferably employed in combination with one or more of other acrylamide compounds.

As the crosslinking agent employable to obtain the polyacrylamide gel membrane, a known crosslinking agent described, for instance, in "Electrophoresis" 1981, 2, 213–228 can be employed singly or in combination. Examples of the crosslinking agents include bifunctional compounds such as N,N'-methylenebisacrylamide (BIS), N,N'-propylenebisacrylamide (PBA), di(acrylamide dimethyl)ether (i.e., N,N'-oxydimethyleneacrylamide), 1,2-diacrylamide ethyleneglycol (DEG), 1,3-diacryloylethyleneurea (EUB), ethylene diacrylate (EDA), N, N'-diallyltartardiamide (DATD), and N,N'-bisacrylylcystamine (BAC). Examples of the crosslinking agents also include trifunctional compounds such as 1,3,5-triacryloylhexahydro-s-triazin, triallylcyanurate, triallylisocyanurate.

The crosslinking agent can be employed in an amount of approx. 0.1 to 30 wt. %, preferably approx. 0.5 to 10 wt. %, based on the total weight of the monomer (i.e., acrylamide compound) and the crosslinking agent. The gel concentration preferably is in the range of approx. 3 to 30 wt/v % (total weight of monomer and crosslinking agent per total volume of gel membrane comprising a monomer, a crosslinking agent and an aqueous medium), the concentration being expressed in accordance with the definition indicated by S. Hjerten in Arch. Biochem. Biophys. 1 (Suppl.), 147 (1962).

The element for electrophoresis of the invention can be employed for analysis of proteins and conjugated proteins (e.g., lipoproteins, glycoproteins, etc.) and the electrophoresis layer (gel membrane) of the element may comprise an anionic surfactant as a modifier. The use of the anionic surfactant is generally essential or preferable for the electrophorectic analyses of proteins or conjugated proteins, because it contributes to perform separation of the protein and conjugated protein and determination of molecular weight of these proteins. However, the electrophoresis layer may not contain the anionic surfactant.

Examples of the anionic surfactant include alkylsulfates, particularly alkysulfates having a long chain alkyl group of at least 10 carbon atoms. The cation contained for formation of the salt generally is an alkali metal ion such as sodium ion, potassium ion, or lithium ion. Sodium ion is preferred from the economical viewpoint The alkylsulfates preferably are dedecylsulfates (salts of sodium, potassium, lithium, etc.), and particularly preferred is sodium dodecylsulfate (SDS). The introduction of SDS into the gel membrane is particularly advantageous for separation of proteins and conjugated proteins, as well as for determination of their molecular weights. The anionic surfactant (modifier) can be contained in the gel-forming solution in an amount of about 0.05 to 2.0 wt/v % (weight per volume of the gel-forming solution), preferably approx. 0.1 to 1.5 wt/v %.

The element for electrophoresis of the invention also can be employed for determination of base sequence of DNA, RNA, their fragments, and their derivatives. For this purpose, a compound containing at least one carbomoyl group is generally incorporated into the electrophoresis medium as a modifier. Examples of the modifier include urea and formamide. Urea is most preferred. The modifier can be used in an amount of approx. 40 to 60 wt. % based on the volume of the aqueous gel containing the monomer and the crosslinking agent. In the case that urea is used as a modifier, the amount generally ranges from approx. 6 moles (approx. 360 g.) per one liter of the aqueous gel containing the monomer and the crosslinking agent to the saturation amount, preferably from about 7 moles (approx. 420 g.) to the saturation amount.

The gel membrane of the invention may contain a water-soluble polymer. As the water-soluble polymer, a water-soluble polymer of the addition polymerization type or condensation polymerization type can be used. Examples of the polymer of the addition polymerization type include non-ionic water-soluble polymers such as polyvinyl alcohol, polyvinyl pyrrolidone, and polyacrylamide. Examples of polymer of the condensation polymerization type include non-ionic water-soluble polyalkylene glycols such as polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferred. The water-soluble polymer is used in a range of approx. 2 to 100 wt. %, preferably, approx. 5 to 50 wt. %, based on the total weight of the monomer and the crosslinking agent.

The addition of a water-soluble polymer serves to impart elasticity to the gel membrane, and thus modified gel membrane is still elastic even if it is dried. Thus the gel membrane is so improved as to be almost free from brittleness, whereby the gel membrane becomes hardly breakable. Further, the viscosity of the gel membrane can be controlled by selecting the molecular weight and amount of the water-soluble polymer.

The gel membrane preferably contains agarose. There is no specific limitation on the agarose to be contained in the gel membrane, and any type of agarose such as low-electroendosmosis agarose, medium-electroendosmosis agarose, or high-electroendosmosis agarose can be used. Examples of agarose employable in the invention include agaroses disclosed in Japanese Patent Provisional Publication Nos. 55(1980)-5730, 55(1980)-110946 (corresponding to U.S. Pat. No 4,290,911 and GB 2 042 571A), 57(1982)-502098 (WO 82/02599, U.S. Pat. No. 4,319,976), etc. The amount of agarose to be added ranges from approx. 0.1 to 2 wt/v%, preferably from approx. 0.3 to 1.2 wt/v%, based on the volume of the aqueous gel containing the monomer and the crosslinking agent. It becomes possible by the addition of agarose that the viscosity of the gel-forming solution can be controlled through changing the temperature of the solution, whereby suppressing flowability of the solution as well as facilitating formation of the gel membrane.

A pH buffer agent can be contained in the gel membrane of the invention.

In the gel membrane of the element for electrophoresis of protein and protein derivatives, a buffer agent which is able to buffer a solution to a range of pH 2.5 to 10.0 can be incorporated. Such buffer agent are described in publications such as "Chemistry Handbook, Fundamental Edition" compiled by The Chemical Society of Japan (Maruzen Ltd., Tokyo, 1966) pp. 1312-1320; "Modern Electrophoresis" edited by Aoki and Nagai (Hirokawa Shoten, 1973), pp. 320-322; "Data for Biochemical Research" compiled by R.M.C. Dawson et al., second edition (Oxford at the Clarendon Press, 1969) pp. 476-508; "Biochemistry" 5, 467 (1966); and "Analytical Biochemistry" 104, pp. 300-310 (1966). Examples of the buffer agents include a buffer agent containing barbital, a buffer agent containing tris(hydroxymethyl)aminomethane (Tris), a buffer agent containing phosphate, a buffer agent containing borate, a buffer agent containing acetic acid or acetate, a buffer agent containing citric acid or citrate, a buffer agent containing lactic acid or lactate, and a buffer agent containing glycine; as well as N,N-bis(2-hydroxyethyl)-glycine (Bicine), N-2-hydroxyethylpiperazine-N'-2-hydroxypropane-3-sulfonic acid (HEPPSO) or its salt, N-2-hydroxyethyylperazine-N'-3-propanesulfonic acid (EPPS) or its salt, N-[(tris(hydroxymethyl)methyl]-3-aminopropanesulfonic acid (TAPS) or its salt. Preferable examples of the buffer agent include potassium dihydrogenphosphate-disodium hydrogenphosphate, Tris-sodium borate, Tris-sodium borate-EDTA·2Na, Tris-citric acid, sodium barbital-sodium acetate, sodium barbital-hydrochloric acid, barbital-sodium barbital, acetic acid-sodium acetate, lactic acid-sodium lactate, citric acid-disodium hydrogenphosphate, Bicine, HEPPSO, sodium salt of HEPPSO, EPPS, sodium salt of EPPS, TAPS, and sodium salt of TAPS.

In the gel membrane of the element of electrophoresis of DNA and the like, a buffer agent which is able to buffer a solution to a range of pH 8.0 to 9.0, preferably pH 8.2 to 8.3 can be incorporated. Such buffer agents are also described in the aforementioned publications.

Examples of the buffer agents include tris(hydroxymethyl)aminomethane (Tris), N,N-bis(2-hydroxyethyl)glycine (Bicine), N-2-hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroymethy)-methyl]-3-aminopropanesulfonic acid (TAPS) or its Na or K salt; as well as an acid, an alkali, and a salt employable in combination with the compounds. Preferable examples of the buffer agents include a combination of Tris and boric acid-EDTA·2Na (pH 8.3).

The gel membrane of the element of the invention is formed by radical crosslinking polymerization between the monomer such as acrylamide with the bi- or trifunctional compound (i.e., crosslinking agent) in an aqueous medium wherein a water-soluble polymer and agarose preferably are dissolved almost homogenously. Thus obtained gel is assumed to have a structure wherein the water-soluble polymer and the agarose are dispersed in the three dimensional crosslinked polymer formed by the reaction of the monomer and crosslinking agent, and the water-soluble polymer and agarose dispersed and entangle with the three dimensionally crosslinked polymer structure.

The crosslinking polymerization can be initiated by a known method, for instance, in the presence of a peroxide and/or under irradiation of ultraviolet rays. The reaction can be further accelerated by heat and irradiation with ultraviolet rays.

As the polymerization catalyst, a known low temperature-polymerization initiator such as those described in "Electrophoresis" 1981, 2, 213 –219, ibid. 1981, 2, 220 –228; and "Modern Electrophoresis" edited by Aoki and Nagai (Hirokawa Shoten, 1973) can be used. Examples of the initiator include a mixture of β-dimethylaminopropionitrile (DMAPN) and ammonium peroxodisulfate, a mixture of N,N,N',N'-tetramethylethylenediamine (TEMED) and ammonium peroxodisulfate, a mixture of TEMED and riboflavin (riboflavin phosphate sodium salt), a combination of a mixture of TEMED, riboflavin and hydrogen peroxide, and irradiation with ultraviolet rays. The radial reaction initiator can be employed in the amount of approx. 0.3 to 5 wt. %, preferably approx. 0.5 to 3 wt. %, based on the total amount of the monomer and crosslinking agent.

The aqueous gel membrane of the element of the invention may contain other additives such as an oxidation inhibitor. The oxidation inhibitor can be chosen from various compounds heretofore known as oxidation inhibitors employable for the gel membrane for electrophoresis. Examples of the oxidation inhibitor include 1,4-dithiothreitol and 2-mercaptoethanol.

A polyol compound such as gylcerol or ethylene glycol can be contained in the aqueous gel membrane of the element of the invention as a wetting agent. The polyol compound can be introduced in an amount of approx. 5 to 40 wt. % based on the volume of the aqueous gel membrane. Glycerol is particularly preferable among the polyol compounds. The addition of the wetting agent serves to keep the gel membrane from excessive dryness possibly caused by evaporation of water during storage of the element, whereby keeping the electrophoresis layer from turning brittle or cracking caused by the excessive dryness. Thus, the improvement of physical properties of the gel membrane is accomplished.

The gel membrane of the element of the invention can be prepared by a process in which a gel forming solution is coated by a known method on an electric insulation plastic film having a smooth surface. The gel forming solution is then crosslinked to polymerization on the surface of the plastic film.

In the case that the gel forming solution is crosslinked on the surface of the plastic film serving as a covering film, the surface of the gel forming solution layer can be covered with a plastic film (including sheet and plate, which serves as a support). As the plastic film, preferably employed is a plastic film provided thereon with an adhesive layer containing gelatin which is one requisite of the element of the invention. The adhesive layer will be descrubed hereinafter in detail. It is also possible to form the plastic film having an adhesive layer on the gel membrane after the crosslinking polymerization of the gel forming solution is complete.

The same material as employable for the plastic film described hereinbefore can be employed as the plastic film to be provided with an adhesive layer thereon. Alternatively, different materials can be also employed. The plastic film to be provided with an adhesive layer thereon may be previously so treated by glow discharge treatment to have a hydrophilic surface.

The adhesive layer provided on the plastic film contains gelatin. The adhesive layer may be a layer of gelatin only or a layer of a mixture of gelatin and other components such as a film-forming component or a filler in the form of fine particles. Gelatin is preferably contained in the adhesive layer in an amount of not less than 5 wt. %, more preferably not less than 10 wt. %. Further, the gelatin preferably exists on the surface of the plastic film in an amount of approx. 3 to 700 mg., more preferably approx. 5 to 500 mg., per 1 m2 of the film. The adhesive layer can be formed on the plastic film by a known process such as a process of applying an adhesive layer-forming solution onto a surface of a plastic film.

As the gelatin employable in the invention, various kinds of known gelatins can be employed. Examples of the gelatin include lime-treated gelatin, acid-treated gelatin and deionized gelatin. They can be employed independently or in combination.

As noted above, the adhesive layer may contain other components such as a film-forming material and a filler in the form of fine particles than the above-described gelatin. These components can be incorporated into the adhesive layer independently or in combination in addition to gelatin.

Examples of the film-forming materials include cellulose derivatives (e.g., nitrocellulose, diacetylcellulose and triacetylcellulose), dextran, agarose, polyacrylamide, polyvinyl alcohol ester (e.g., polyvinyl acetate), polyacrylate ester (e.g., poly-[hydroxyethylacrylate]), pullulan, pullulan derivatives, polyvinylidene chloride, vinylidene chloride latex and water glass.

Examples of the fillers in the form of fine particles include fine particles of silica such as colloidal silica and methanol silica, fine particles of titanium dioxide, fine particles of alumina, and polymer beads.

The element for electrophoresis of the invention can be prepared by first forming a gel membrane on a plastic film not provided with an adhesive layer, and then providing other plastic film provided with an adhesive layer on the gel membrane, as described above. Otherwise, it is also possible to prepare an element of the invention by a process comprising the steps forming a gel membrane on the adhesive layer which is provided on a plastic film and then providing other plastic film not having an adhesive layer on the gel membrane.

Thus, the element for electrophoresis consisting of a plastic film, an medium layer for electrophoresis, an adhesive layer containing gelatin and a plastic film can be prepared.

The element for electrophoresis of the invention can be employed for the horizontal or vertical electrophoresis, disc electrophoresis, etc. by known methods seen, for instance, in the aforementioned texts.

The present invention will be more clearly understood with reference to the following examples.

EXAMPLES 1-6

To 100 ml of an aqueous solution containing 7.8 g. of acrylamide, 0.2 g. of BIS, 3.58 g. of disodium hydrogen phosphate 12 hydrates, 0.33 g. of sodium dihydrogenphosphate 2 hydrates, 0.10 g. of sodium dodecylsulfate (SDS) and 1.08 g. of tris(hydroxymethyl) aminomethane were added 1.3 ml of ammonium peroxodisulfate (5 weight %), 33 $\mu$l of TEMED and 10 mg. of riboflavin phosphate sodium salt as polymerization initiators. The mixture was coated on a thick polyethylene terephthalate film of 175 $\mu$m thick to give a layer of the coated mixture having thickness of 0.2 mm, and the coated layer was subjected to crosslinking polymerization by irradiation with ultraviolet rays in a nitrogen atmosphere, to form an polyacrylamide gel membrane on the film.

The gel membrane prepared as above was covered with a thin polyethylene terephthalate film of 63 $\mu$m thick provided with an adhesive layer having the composition set forth in Table 1, to prepare elements for electrophoresis.

TABLE 1

| | Composition of Adhesive layer |
|---|---|
| Example 1 | lime-treated gelatin (0.01 g/m$^2$) |
| Example 2 | lime-treated gelatin (0.1 g/m$^2$) |
| Example 3 | lime-treated gelatin (0.03 g/m$^2$) and nitrocellulose (0.17 g/m$^2$) |
| Example 4 | lime-treated gelatin (0.03 g/m$^2$) and acetylcellulose (0.17 g/m$^2$) |
| Example 5 | lime-treated gelatin (0.03 g/m$^2$) and vinylidene chloride latex (0.17 g/m$^2$) |
| Example 6 | lime-treated gelatin (0.03 g/m$^2$) and methanol silica (0.17 g/m$^2$) |

COMPARISON EXAMPLE 1

The procedure of Example 1 was repeated except for covering the gel membrane with the thin PET film not provided with an adhesive layer (i.e., film having no adhesive layer), to prepare an element for electrophoresis.

EVALUATION ON ADHESIVENESS

The elements obtained in Examples 1 to 6 and Comparison Example 1 were evaluated on adhesiveness between the gel membrane and the thin film in the following manner. The element was allowed to stand for one day, and the thick PET film having no adhesive layer was removed from the element. With respect to the elements of Examples 1 to 6, the gel membrane was completely bound to the thin PET film having an adhesive layer. However, the gel membrane of the element obtained in Comparison Example 1 was separated together with the thick film from the thin film.

Further, after the thick film (having no adhesive layer) was removed from each element obtained in Examples 1 to 6, the element was immersed in an aqueous Coomasie Blue R-250 (Colour Index Constitution No. 42660) solution (0.1 %) for dyeing. In the dyeing process, the gel membrane was not separated from the another film.

EXAMPLES 7-12

To 100 ml of an aqueous solution containing 7.85 g. of acrylamide, 0.2 g. of BIS, 0.15 g. of 1,3,5-triacryloylhexahydro-s-triazine, 0.3 g. of agarose (low-electroendosmosis, gelling temperature 36° C.), 1.0 g. of polyacrylamide, 3.58 g. of disodium hydrogenphosphate 12 hydrates, 0.33 g. of sodium dihydrogenphosphate 2 hydrates and 0.10 g. of SDS were added 1.3 ml of ammonium peroxodisulfate (5 weight %), 33 $\mu$l of TEMED and 10 mg. of riboflavin phosphate sodium salt as polymerization initiators. The mixture was coated on a thick polyethylene terephthalate film of 175 $\mu$m thick to give a layer of the coated mixture having thickness of 0.2 mm, and the coated layer was subjected to crosslinking polymerization by irradiation with ultraviolet rays in a nitrogen atmosphere, to form an polyacrylamide gel membrane on the film.

Then, slots for sample inlet were formed at the end of the gel membrane in the conventional manner. The gel membrane was then covered with a thin polyethylene terephthalate film of 63 $\mu$m thick provided with an adhesive layer having the composition set forth in Table 1, to prepare element for electrophoresis.

A control (standard) protein was electrophoresed using the elements. After the thick film having no adhesive layer was removed, the element was immersed in an aqueous Coomasie Blue R-250 solution (0.1 %) for dyeing. It was confirmed that the gel membrane was not separated from the thin film having an adhesive layer in the dyeing process. Also confirmed was that the electrophoretic pattern on each membrane was satisfactory.

EXAMPLES 13-18

On a surface of a thin polyethylene terephthalate film of 63 $\mu$m thick was formed an adhesive layer having the composition set forth in Table 1.

Independently, to 100 ml of an aqueous solution containing 5.8 g. of acrylamide, 0.20 g. of BIS, 1.08 g. of tris(hydroxymethyl) aminomethane, 0.55 g. of boric acid, 93 mg. of EDTA·Na salt and 20 g. of glycerol were added 1.3 ml of ammonium peroxodisulfate (5 weight %) and 33 $\mu$l of TEMED as polymerization initiators.

The mixture was coated on the above-obtained adhesive layer provided on the thin film to give a layer of the coated mixture having thickness of 1 mm, and the coated layer was subjected to crosslinking polymerization by irradiation with ultraviolet rays in a nitrogen atmosphere, to form an polyacrylamide gel membrane on the adhesive layer.

Then, slots for sample inlet were formed at the end of the gel membrane in the conventional manner. The gel membrane was then covered with a thick polyethylene terephthalate film of 175 $\mu$m thick provided with no adhesive layer, to prepare elements for electrophoresis.

Plasmid pBR-322 of Escherichia coli was treated by a restriction enzyme AsuI and then resolved on the gel membrane of the above element. After the thick film having no adhesive layer was removed from the element, the element was dyed with ethidium bromide. It was confirmed that the gel membrane was not separated from the thin film having an adhesive layer in the dyeing process. Also confirmed was that the DNA resolved pattern on the gel membrane was satisfactory.

EXAMPLES 19-24

To 100 ml of an aqueous solution containing 7.8 g. of acrylamide, 0.2 g. of BIS, 42 g. of urea, 1.08 g. of tris(-hydroxymethyl)aminomethane, 0.55 g. of boric acid and 93 mg. of EDTA·Na salt were added 1.3 ml of ammonium peroxodisulfate (5 weight %), 33 μl of TEMED and 10 mg. of riboflavin phosphate sodium salt as polymerization initiators. The mixture was coated on a thick polyethylene terephthalate film of 175 μm thick to give a layer of the coated mixture having thickness of 0.2 mm, and the coated layer was subjected to crosslinking polymerization by irradiation with ultraviolet rays in a nitrogen atmosphere, to form an polyacrylamide gel membrane on the film.

The gel membrane prepared as above was covered with a thin polyethylene terephthalate film of 63 μm thick provided with an adhesive layer having the composition set forth in Table 1, to prepare elements for eletrophoresis.

COMPARISON EXAMPLE 2

The procedure of Example 19 was repeated except for using a thin film not provided with an adhesive layer, to prepare an element for electrophoresis.

EVALUATION ON ADHESIVENESS

The elements obtained in Examples 19 to 24 and Comparison Example 2 were evaluated on adhesiveness between the gel membrane and the thin film in the following manner. The element was allowed to stand for one day, and the thick film was removed from the element. With respect to each of the elements of Examples 19 to 24, the gel membrane was completely bound to the thin film having an adhesive layer. However, the gel membrane of the element obtained in Comparison Example 2 was separated together with the thick from the thin film.

Further, after the support was removed from each element obtained in Examples 19 to 24, the element was immersed in an aqueous acetic acid (10 %) solution. In the process, the gel membrane was not separated from the thin film.

EXAMPLES 25-30

To 100 ml of an aqueous solution containing 7.8 g. of acrylamide, 42 g. of urea, 0.15 g. of 1,3,5-triacryloylhexahydro-s-triazine, 0.3 g. of agarose (low-electroendosmosis, gelling temperature 36° C.), 1.0 g. of polyacrylamide, 1.08 g. of tris(hydroxymethyl)aminomethane, 0.55 g. of boric acid and 93 mg. of EDTA·Na salt were added 1.3 ml of ammonium peroxodisulfate (5 weight %), 33 μl of TEMED and 10 mg. of riboflavin phosphate sodium salt as polymerization initiators. The mixture was coated on a thick polyethylene terephthalate film of 175 μm thick to give a layer of the coated mixture having thickness of 0.2 mm, and the coated layer was subjected to crosslinking polymerization by irradiation with ultraviolet rays in a nitrogen atmosphere, to form an polyacrylamide gel membrane on the film.

Then, slots for sample inlet were formed at the end of the gel membrane in the conventional manner. The gel membrane was then covered with a thin polyethylene terephthalate film of 63 μm thick provided with an adhesive layer having the composition set forth in Table 1, to prepare elements for electrophoresis.

Samples (32P-DNA cleaved by Maxam-Gilbert method and a sample prepared by Sanger method) were electrophoresed or the polyacrylamide gel membrane for sequencing the film of the element was removed and then the gel membrane was immersed in an aqueous acetic acid (10%) solution for fixing the DNA. The gel membrane was dried and subjected to a conventional autoradiographic process. It was confirmed that a highly resolved electrophoretic pattern was formed on the gel membrane with respect to each sample.

EXAMPLES 31-36

The procedures of Examples 19 to 24 were repeated except for varying thickness of the thin film to 25 μm, to prepare elements for electrophoresis.

COMPARISON EXAMPLE 3

The procedure of Example 31 was repeated except for using a thin film having no adhesive layer, to prepare an element for electrophoresis.

EVALUATION ON ADHESIVENESS

The elements obtained in Examples 31 to 36 and Comparison Example 3 were evaluated on adhesiveness between the gel membrane and the thin film in the following manner. The element was allowed to stand for one day, and the thick film was removed from the element. With respect to the elements of Examples 31 to 36, the gel membrane was completely bound to the thin film having an adhesive layer. However, the gel membrane of the element obtained in Comparison Example 3 was separated together with the thick film from the thin film.

Further, after the thick film was removed from each element obtained in Examples 31 to 36, the element was immersed in an aqueous acetic acid (10 %) solution. It was confirmed that the gel membrane was not separated from the thin film in the process.

EXAMPLES 37-42

The procedures of Examples 25 to 30 were repeated except for varying thickness of the thick film to 25 μm, to prepare elements for electrophoresis.

The obtained elements were subjected to the same electrophoresis and the same subsequent treatments as described in Example 25. Then the gel membrane of the element was subjected to a conventional autoradiographic process. It was confirmed that a highly resolved electrophoretic pattern was formed on the gel membrane for each sample.

We claim:

1. An element for electrophoresis comprising:
   (I) a plastic film;
   (II) a layer for electrophoresis comprising an aqueous polyacrylamide gel formed by crosslinking polymerization of an acrylamide compound and a crosslinking agent in the presence of water;
   (III) an adhesive layer containing gelatin; and
   (IV) a plastic film, which are superposed in order.

2. The element for electrophoresis as claimed in claim 1, wherein said gelatin contained in the adhesive layer is a lime-treated gelatin.

3. The element for electrophoresis as claimed in claim 1, wherein the adhesive layer consisting essentially of gelatin.

4. The element for electrophoresis as claimed in claim 1, wherein said adhesive layer contains at least 5 wt. % of gelatin and further contains a film-forming material.

5. The element for electrophoresis as claimed in claim 1, wherein said adhesive layer contains at least 5 wt. % of gelatin and further contains a material selected from the group consisting of cellulose derivatives, dextran, agarose, polyacrylamide, polyvinyl alcohol esters, polyacrylate esters, pullulan, pullulan derivatives, polyvinylidene chloride, vinylidene chloride latex and water glass.

6. The element for electrophoresis as claimed in claim 1, wherein said adhesive layer contains at least 5 wt. % of gelatin and further contains a filler of fine particles.

7. The element for electrophoresis as claimed in claim 1, wherein said adhesive layer contains at least 5 wt. % of gelatin and further contains colloidal silica or methanol silica.

8. The element for electrophoresis as claimed in claim 1, wherein said medium layer contains a compound having at least one carbamoyl group.

9. The element for electrophoresis as claimed in claim 1, wherein said medium layer contains urea or formamide.

10. The element for electrophoresis as claimed in claim 1, wherein said medium layer contains a water-soluble polymer and agarose.

11. The element for electrophoresis as claimed in claim 1, wherein said medium layer contains an anionic surfactant.

12. The element for electrophoresis as claimed in claim 1, wherein said medium layer contains an alkylsulfate.

13. The element for electrophoresis as claimed in claim 1, wherein the plastic film (I) is thicker than the plastic film (IV).

* * * * *